(12) United States Patent
Tandon et al.

(10) Patent No.: US 7,764,382 B2
(45) Date of Patent: Jul. 27, 2010

(54) ILLUMINATOR FOR SPECULAR MEASUREMENTS

(75) Inventors: Jagdish Tandon, Fairport, NY (US); Robert Herloski, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 94 days.

(21) Appl. No.: 12/014,361

(22) Filed: Jan. 15, 2008

(65) Prior Publication Data
US 2009/0180111 A1 Jul. 16, 2009

(51) Int. Cl.
*G01N 21/55* (2006.01)
(52) U.S. Cl. .................. 356/445; 250/216; 355/41; 355/70
(58) Field of Classification Search .............. 356/237.5, 356/445; 382/154; 250/216
See application file for complete search history.

(56) References Cited

U.S. PATENT DOCUMENTS

| | | | | |
|---|---|---|---|---|
| 5,636,025 A | * | 6/1997 | Bieman et al. ............... 356/619 |
| 6,522,777 B1 | * | 2/2003 | Paulsen et al. ............... 382/154 |
| 6,975,949 B2 | * | 12/2005 | Mestha et al. ................. 702/76 |
| 7,072,034 B2 | * | 7/2006 | Rosengaus et al. ....... 356/237.5 |
| 7,215,418 B2 | * | 5/2007 | Gahagan et al. .......... 356/237.2 |
| 7,544,923 B1 | * | 6/2009 | Herloski et al. ............. 250/216 |
| 2008/0062406 A1 | * | 3/2008 | Finarov et al. ................. 356/73 |
| 2008/0245979 A1 | * | 10/2008 | Banton et al. ............ 250/559.4 |

* cited by examiner

*Primary Examiner*—Tarifur R. Chowdhury
*Assistant Examiner*—Isiaka O Akanbi
(74) *Attorney, Agent, or Firm*—Pillsbury Winthrop Shaw Pittman LLP

(57) ABSTRACT

A system for detecting reflectance from an image bearing surface in a printer or electronic copier includes an illuminator array, positioned adjacent to the image bearing surface, comprising a plurality of discrete illuminator elements that are spaced in a linear arrangement; a lens array comprising a plurality of collimator lenses positioned between the illuminator array and the image bearing surface, the collimator lenses being positioned with respect to the illuminator array to receive light beams emitted by the illuminator elements and to collimate the light beams for transmission to the image bearing surface at an incidence angle; a linear sensor array comprising a plurality of sensors and positioned adjacent to the image bearing surface such that, of the light beams reflecting off the image bearing surface, specular portions and diffuse portions reflecting at a reflectance angle are received by the sensors.

16 Claims, 5 Drawing Sheets

ILLUMINATOR FOR SPECULAR MEASUREMENTS

FIELD

This present disclosure relates to a system for providing specular reflectance of an image bearing surface in a printer.

BACKGROUND

Defects in the subsystems of a xerographic, electrophotographic or similar image forming system, such as a laser printer, digital copier or the like, may give rise to visible streaks in a printed image. Streaks are primarily one-dimensional defects in an image that run parallel to the process (or slow scan) direction. In a printing system, an image input module is used to measure reflection from an image bearing surface and from test patches on the image bearing surface. Often, these image input modules are referred to as densitometers, as they are imaging the image bearing surface to detect the toner deposition or lack thereof on the image bearing surface. These measured reflections are used in a streak correction methodology in the printer.

In prior systems, the image input module uses a fluorescent lamp or a rare gas lamp for illuminating the image bearing surface and the test patches. The fluorescent lamp or the rare gas lamp used for illumination is a continuous source of light in the cross-process (or fast scan) direction. However, the fluorescent lamp or the rare gas lamp is relatively expensive.

SUMMARY

In an embodiment, a system for detecting reflectance from an image bearing surface in a printer or electronic copier is provided. The system includes an illuminator array, a lens array that includes a plurality of collimator lenses and a linear sensor array. The illuminator array, positioned adjacent to the image bearing surface, includes a plurality of discrete illuminator elements spaced in a linear arrangement, where the illuminating elements are each configured to emit a light beam. The lens array, which includes a plurality of collimator lenses, is positioned between the illuminator array and the image bearing surface. The collimator lenses are positioned with respect to the illuminator lens to receive the light beams emitted by the illuminator elements and to collimate the light beams for transmission to the image bearing surface at an incidence angle. The linear sensor array includes a plurality of sensors positioned adjacent to the image bearing surface such that specular portions and diffuse portions of the collimated light beams reflecting off the image bearing surface at a reflectance angle are received by the sensors.

In another embodiment, a method for detecting reflectance from an image bearing surface in a printer or electronic copier is provided. The method includes positioning an illuminator array with a plurality of discrete illuminator elements spaced in a linear arrangement adjacent to the image bearing surface and configuring the illuminator elements to emit a light beam; positioning a lens array with a plurality of collimator lenses between the illuminator array and the image bearing surface; positioning the collimator lenses with respect to the illuminator array to receive the light beams emitted by the illuminator elements and to collimate the lights beams for transmission to the image bearing surface at an incidence angle; positioning a linear sensor array comprising a plurality of sensors adjacent to the image bearing surface, such that specular portions and diffuse portions of the collimated light beams reflecting off the image bearing surface at a reflectance angle are received by the sensors.

Other aspects, features, and advantages will become apparent from the following detailed description, and the accompanying drawings.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

The law of reflection states that the direction of a specular component of the outgoing reflected light and the direction of incoming light make the same angle with respect to the surface normal. That is, the angle of incidence is equal to the angle of reflectance. Specular reflection is the mirror-like reflection of light from a surface, in which light from a single incoming direction is reflected into a single outgoing direction. In contrast, diffuse reflection is reflection of light from a surface, in which light from a single incoming direction is reflected in many directions, due to surface irregularities that cause the rays of light to reflect in different outgoing directions. The type of reflection depends on the structure of the surface. For example, in a printer, the area on the image bearing surface that is covered by the toner exhibits a higher proportion of diffuse reflection, while the area on the image bearing surface that is not covered by the toner exhibits a higher proportion of specular reflection.

Figure 1:
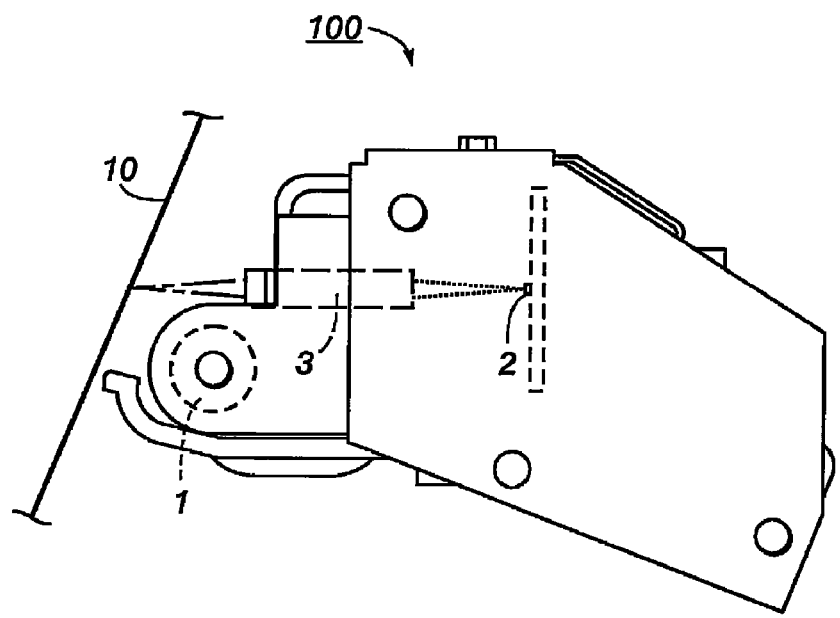
FIG. 1 is a cross sectional view of an image input module used in a printer.

FIG. 1 shows a cross section of an image input module used in a printer. An image input module 100 in the printer is used to measure reflection from an image bearing surface 10 and from test patches on the image bearing surface 10. Test patches are predetermined patches of toner periodically transferred to the image bearing surface for calibration purposes. By imaging the test patches, the printer can evaluate each printed test patch against its optimal characteristics, and make adjustments to its toner deposition functionality of its print engine accordingly.

The printer generally has two important dimensions: the process (or slow scan) direction and the cross-process (or fast scan) direction. The direction in which the image bearing surface moves is referred to as process (or slow scan) direction, and the direction in which the plurality of sensors are oriented is referred to as cross-process (or fast scan) direction. The cross-process (or fast scan) direction is generally perpendicular to the process (or slow scan) direction.

Figure 6:
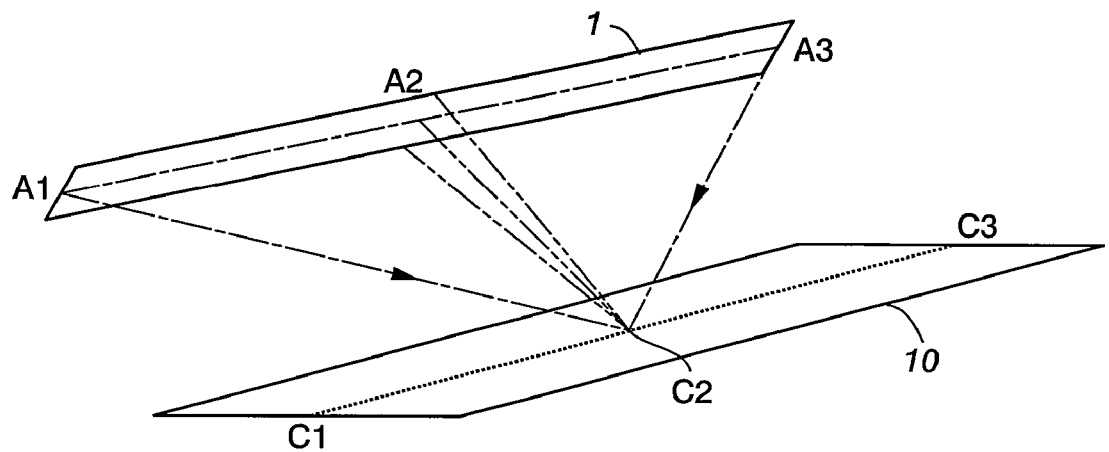
FIG. 6 is an illustration illustrating transmission of light between a image bearing surface and an illuminator.
Figure 7:
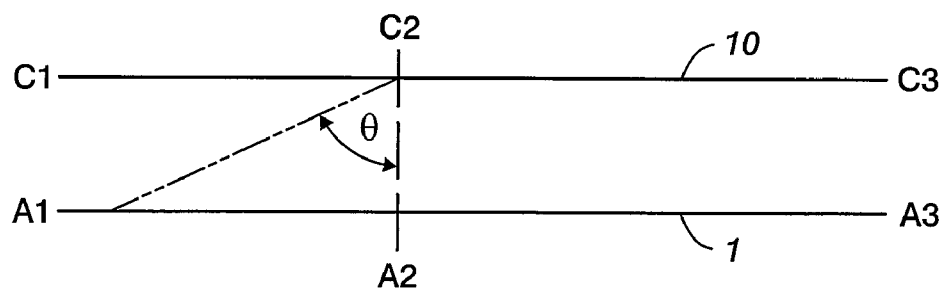
FIG. 7 is an illustration illustrating the Plane A1A3C3C1 of FIG. 6.

The image input module 100 comprises an illuminator 1, lens 3 (such as a self-focusing gradient index lens, e.g., a Selfoc® lens) and an image sensor 2. The angular distribution of light produced by the illuminator 1 at the image bearing surface 10 can vary in the fast scan direction, depending upon the illuminator architecture, particularly in the case of discrete light sources such as LEDS. Referring to FIGS. 6 and 7, under specular conditions, the light received by the image sensor depends upon the angular acceptance angle of the imaging lens. The angular acceptance angle of the imaging lens can be expressed as $\pm\alpha$, where a may be 5°, 10°, or other predefined angle which is a fixed property of the lens. In general, light that is incident at an angle of $\leq \pm\alpha$ relative to the normal to the image bearing surface (in the fast scan direction) will, under specular reflection conditions, be reflected at an angle of $\leq \pm\alpha$ relative to the optical axis of the imaging lens and will be captured by the imaging lens and transmitted to the image sensor. Light outside that range of angles will not be transmitted by the lens. At the fast scan locations above, or nearly above, an LED, there is a significant portion of light with an angular distribution within the acceptance angle of the lens, and the specular reflected light is transmitted to the image sensor. However, between LEDs, if the gap is large enough, the only light incident on the image bearing surface has an angular distribution greater than the acceptance angle of the lens, and hence is not transmitted to the image sensor.

By modifying the angular distribution of light from the light source(s), more of the specular light from the light source can be brought into the acceptance angle of the imaging lens.

In addition, the image input module 100 is sensitive to the uniformity of the illumination. Since the image input module 100 measures both the specular reflection from the image bearing surface 10, which is an indication of the area that is not covered by the toner, and the diffuse reflection from the toner on the image bearing surface 10, which is an indication of the area that is covered by the toner, an important parameter to detect is the nonuniformity of the specular to diffuse ratio (on a pixel by pixel basis). The specular reflectance from the image bearing surface is the desired signal in these measurements while the diffuse reflectance from the toner on the image bearing surface is an unwanted signal. Therefore, it is desirable to maximize the specular component in relation to the diffuse component in the optical system of the image input module.

The specular reflectance is also particularly useful for the halftone masking of the image bearing surface. Halftone technique simulates continuous tone imagery through the use of dots of varying colorations. In halftone techniques, the density of colored patterned dots (usually from the four patterned primary colors, cyan, magenta, yellow and black), are varied to reproduce any particular shade. Therefore with halftone, the patches have dots with toner and blank areas between these dots. If the patches are more dense, i.e., more dots per area coverage, then the specular signal received from the image bearing surface 10, which is an indication of the blank areas that is not covered by the toner, is weaker. On the other hand, if the patches are less dense, i.e., less dots per area coverage, then the specular signal received from the image bearing surface 10, which is an indication of the blank areas that is not covered by the toner, is stronger. Thus, the specular reflectance can provide information about the blank areas between the dots.

The uniformity of the illumination exiting the illuminator array 1 is improved by using an array of collimating lenses to create a curtain of light concentrated in the direction of the image bearing surface. The collimating lenses are placed in the optical path of the illuminator maximizes the specular illumination by bringing more of the specular light from the illuminator into the acceptance angle of the imaging lens. The collimation of the illuminator helps to insure more sharply defined specular image capture. Also, by using the collimating lenses the diffuse signal detected by the sensor remains unchanged but the specular signal detected by the sensor is increased.

The collimating lenses transforms divergent beams of the light from an illuminator array into a thin beam of parallel rays. The collimating lenses are also characterized by an operative focal length. The focal length is defined as a distance from the illuminator array at which the collimating lenses must be positioned in order to properly collimate light emanating from the illuminator array.

Figure 2:
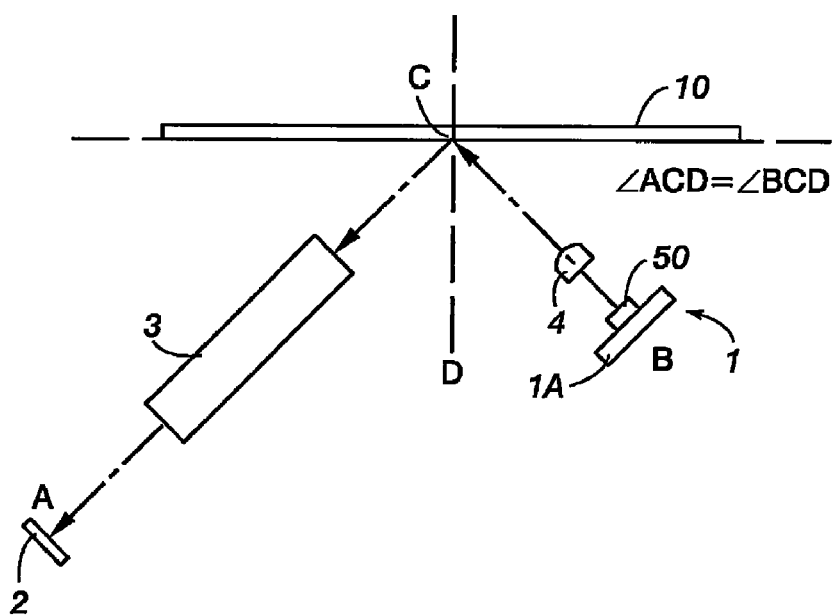
FIG. 2 shows an embodiment, having an illuminator, a collimator lens, a linear sensor array.

FIG. 2 shows an LED illumination system for a specular-mode imager using an array of collimating lenses. The system has an illuminator array 1, a image bearing surface 10, a lens array 4 comprising plurality of collimator lenses, a lens array 3, a linear sensor array 2.

The illuminator array 1 has a plurality of discrete illuminator elements that are spaced in a linear arrangement. In one embodiment, the LEDs are placed on a board 1A. Preferably, the illuminator elements are LEDs that are equally spaced at regular intervals. In one embodiment, the LEDs are spaced about every 4 mm apart in the fast scan direction. In another embodiment, the linear LED array could also use more than one row of LEDs. The combination of a linear array sensor and linear LED array allows for high spatial resolution (e.g., 600 spots per inch) in both the process and cross-process directions. The LED arrays could be all one color, e.g., white or of multiple colors, as described in U.S. Pat. No. 6,975,949, incorporated herein by reference. Though very small LEDs provide a higher level of collimation, larger LEDs may be used in this system in order to reduce sensitivity to component placement tolerances. Other discrete light sources are also contemplated, such as fiber optic light guide tubes. The image bearing surface 10 used in the system is on a photoreceptor comprising a belt or a drum configuration.

The lens array 4 having plurality of collimator lenses is positioned between the illuminator array 1 and the image bearing surface 10. The collimator lenses are positioned with respect to the illuminator array 1 to receive the light beams emitted by the illuminated elements of the illuminator array 1. The collimator lenses collimate the light beams emitted by the illuminated elements of the illuminator array 1 for transmission to the image bearing surface 10 at an incidence angles θ, where the incidence angles θ is less than a predetermined acceptance angle α of the lens array 3. The collimating lenses can be made of any light transparent material, such as plastics or glass.

The lens array 3, such as a Selfoc® lens or other microlens arrangement with the predetermined acceptance angle α, is interposed between the image bearing surface 10 and the linear sensor array 2. A Selfoc® lens is a gradient index lens which consists of fiber rods with parabolic index profile. In one embodiment, the Selfoc® lens has an acceptance angle α of about ±9 degrees.

Preferably, the linear sensor array 2 is, for example, a full width array (FWA) sensor. A full width array sensor is defined as a sensor that extends substantially an entire width (perpendicular to a direction of motion) of the moving image bearing surface. The full width array sensor is configured to detect any desired part of the printed image, while printing real images. The full width array sensor may include a plurality of sensors equally spaced at intervals (e.g., every 1/600th inch (600 spots per inch)) in the cross-process (or fast scan) direction. See for example, U.S. Pat. No. 6,975,949, incorporated herein by reference. It is understood that other linear array sensors may also be used, such as contact image sensors, CMOS array sensors or CCD array sensors.

In one embodiment, the sensor array 2 includes a specular reflectance sensor array and a diffuse reflectance sensor array as discussed in detail in U.S. patent application Ser. No. 11/783,174), herein incorporated by reference.

The illuminator array 1 is located on a line B-C and is configured to emit a light beam that passes through the collimator lenses of the lens array 4. The collimator lenses of the lens array 4 are also located on the line B-C. The light beams from the collimator lenses of the lens array 4 are incident onto the image bearing surface 10 at point C, which is reflected, thereby producing generally specular reflectance in a first direction along line C-A, and some generally diffuse reflectance. The angle (IACD) between line A-C and normal line D-C is substantially equal to the angle (ZBCD) between line B-C and normal line D-C, such that the illuminator array 1 is configured to emit a light beam onto the image bearing surface 10 at point C, thereby producing a generally specular reflectance from the image bearing surface 10 at a specular reflectance angle along line A-C. The linear sensor array 2 is positioned adjacent to the image bearing surface 10 and is located along line A-C, such that it captures the generally specular portion and the generally diffuse portion of the collimated light beam reflecting off the image bearing surface 10 at a specular reflectance angle at point C. This embodiment provides full resolution images for both types of reflected light. A calibration procedure could be determined so that the signals from the linear sensor array 2 can be used to work out the true specular reflectance and the difference between the specular and diffuse reflectances of the image being measured. For example, the amount of diffuse light being reflected at the specular angle may be determined and the subsequent specular sensor readings may be corrected by subtracting a fraction of the diffuse sensor signal from the specular sensor signal as discussed in U.S. patent application Ser. No. 11/944,243, herein incorporated by reference. Line C-D represents a normal line to the surface at a point C of the image bearing surface 10. Point C may actually be a line or region on the surface of the image bearing surface 10.

Figure 3:
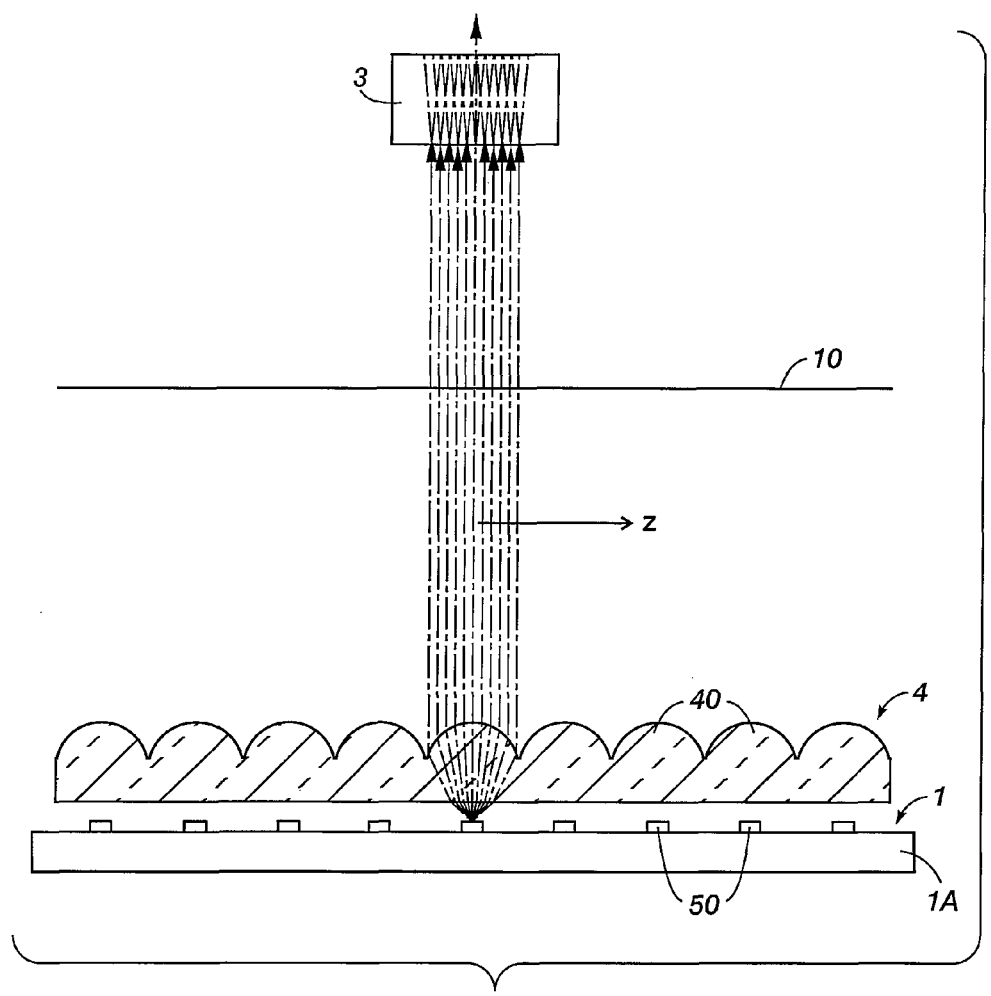
FIG. 3 shows an exploded view of the LED illumination system using an array of collimating lenses.

FIG. 3 shows the illuminator array with collimator lenses. The collimating lenses 40 can be used with light emitting diodes 50 to transmit fairly collimated irradiance onto the image bearing surface 10. For clarity, only one LED is shown with ray tracing turned on. A collimated light beam yields a greater specular to diffuse ratio. The collimator lenses maximize the ratio of specular reflection from the image bearing surface 10 to the diffuse reflection from the toner on the image bearing surface 10. For a specular reflection, only the light that is incident within the acceptance angle of the lens contributes to usable specular signal whereas light incident at any angle on the image bearing surface contributes to the diffuse signal. Thus, all incident light that contributes to specular signal also contributes to diffuse signal. However, all incident light that contributes to diffuse signal does not contribute to specular signal.

A collimation factor, C, can be defined by the following equation $$C = \frac{\int_{\theta=0}^{\theta=\alpha} i(\theta)\,d\theta}{\int_{\theta=0}^{\theta=90} i(\theta)\,d\theta}$$

Where:

$\theta$=angle of incidence at a point on the image bearing surface 10

$\alpha$=acceptance angle of the lens 3

$i(\theta)$=irradiance at angle $\theta$ on the image bearing surface plane

In a highly collimated system, C approaches 1.

Referring now to FIGS. 6 and 7, the irradiance at point C2 on the image bearing surface 10 consists of integration of rays at all values of angle $\theta$. For diffuse reflection from toner on the image bearing surface 10 the useful value of $\theta$ can vary from 0 to 90 degrees but for specular reflection off the image bearing surface 10, the useful value of $\theta$ is limited by the lens 3 acceptance angle $\alpha$.

Figure 4:
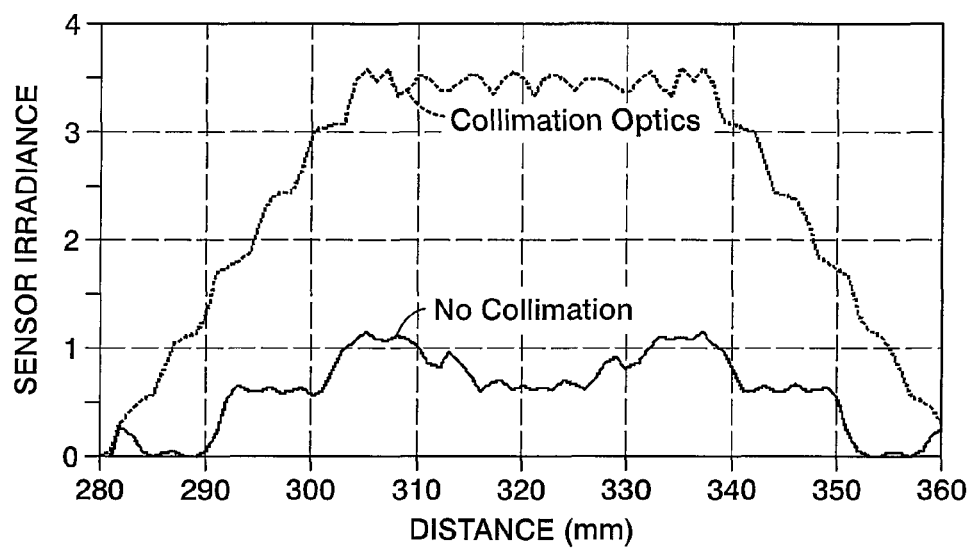
FIG. 4 shows computer simulation graph illustrating the specular signal, both with and without the collimator lenses.
Figure 5:
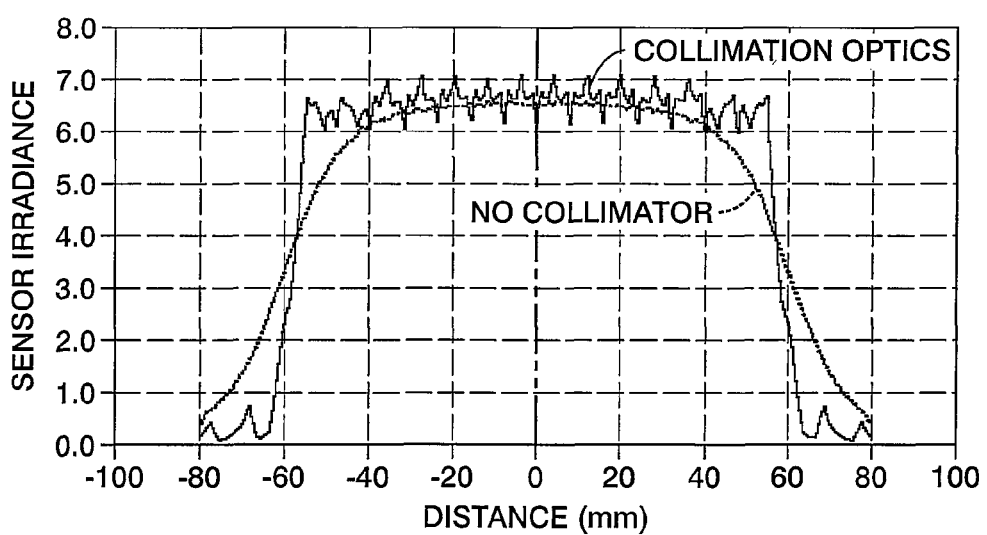
FIG. 5 shows computer simulation graph illustrating the diffuse signal, both with and without the collimator lenses.

FIGS. 4 and 5 are computer simulation graphs illustrating the specular irradiance and diffuse irradiance, both with and without the collimator lenses, respectively.

FIG. 4 is a graph illustrating the simulation results for the calculated sensor irradiance, both with and without the collimating lenses. Collimation lenses significantly increase the magnitude of the specular irradiance. Graph illustrates the distance in millimeters on a horizontal x-axis. On a vertical y-axis, the graph illustrates specular irradiance in arbitrary units. The noise or ripples in the profiles is due to the limited number of rays traced.

FIG. 5 is a graph illustrating the simulation results for the calculated diffuse irradiance, both with and without the collimating lenses. This graph illustrates the distance in millimeters on a horizontal x-axis. On a vertical y-axis, the graph illustrates diffuse irradiance in arbitrary units. The noise or ripples in the profiles is due to the limited number of rays traced. The diffuse irradiance in the center of the plot is roughly the same, both with and without the collimating lenses.

From these simulation results, since the diffuse h-radiance is approximately the same for both with and without the collimator lenses, both the specular to diffuse ratio and the specular irradiance have improved by a factor. In one embodiment, the factor was approximately 3.5. Thus, the use of collimated lenses provides larger specular component and improved radiometry.

A processor (not shown) is provided to both calibrate the sensor and to process the reflectance data detected by the linear sensor. It could be dedicated hardware like ASICs or FPGAs, software, or a combination of dedicated hardware and software. For the different applications the basic algorithm for extracting the specular and diffuse components would be the same but the analysis for the particular applications would vary.

Figure 8:
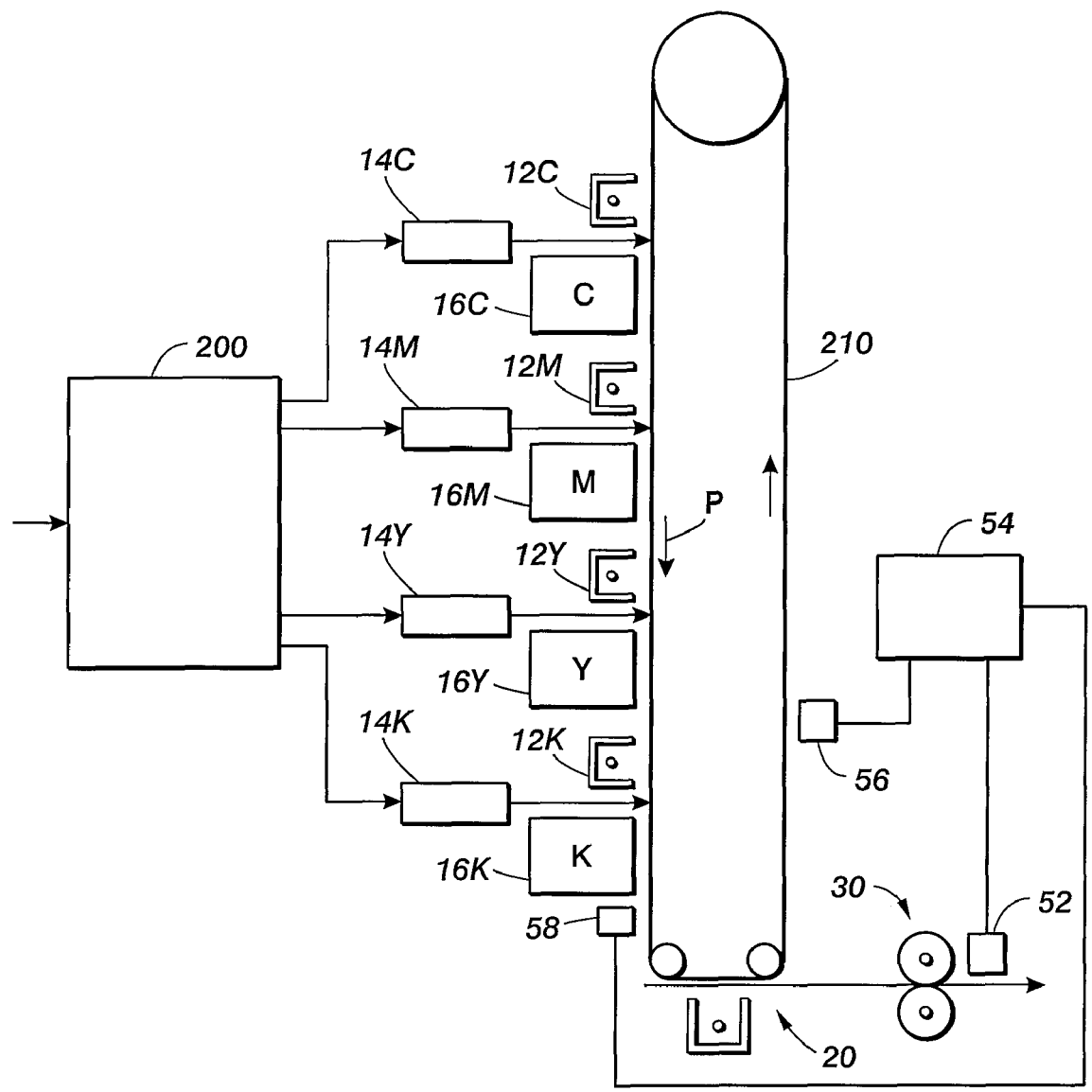
FIG. 8 is a simplified elevational view of basic elements of a xerographic color printer, showing a context of the various embodiments.

FIG. 8 is a simplified elevational view of basic elements of a color printer, showing a context of the present disclosure. Specifically, there is shown an "image-on-image" xerographic color printer, in which successive primary-color images are accumulated on a photoreceptor belt, and the accumulated superimposed images are in one step directly transferred to an output sheet as a full-color image. In one implementation, the Xerox Corporation iGen3® digital printing press may be utilized. However, it is appreciated that any printing machine, such as monochrome machines using any technology, machines which print on photosensitive substrates, xerographic machines with multiple photoreceptors, or ink-jet-based machines, can beneficially utilize the present disclosure as well.

Specifically, the FIG. 8 embodiment includes a belt photoreceptor 210, along which are disposed a series of stations, as is generally familiar in the art of xerography, one set for each primary color to be printed. For instance, to place a cyan color separation image on photoreceptor 210, there is used a charge corotron 12C, an imaging laser 14C, and a development unit 16C. For successive color separations, there is provided equivalent elements 12M, 14M, 16M (for magenta), 12Y, 14Y, 16Y (for yellow), and 12K, 14K, 16K (for black). The successive color separations are built up in a superimposed manner on the surface of photoreceptor 210, and then the combined full-color image is transferred at transfer station 20 to an output sheet. The output sheet is then run through a fuser 30, as is familiar in xerography.

Also shown in the FIG. 8 is a set of what can be generally called "monitors," such as 56 and 52, which can feed back to a control device 54. The monitors such as 56 and 52 are devices which can make measurements to images created on the photoreceptor 210 (such as monitor 56) or to images which were transferred to an output sheet (such as monitor 52). These monitors can be in the form of optical densitometers, calorimeters, electrostatic voltmeters, etc. There may be provided any number of monitors, and they may be placed anywhere in the printer as needed, not only in the locations illustrated. The information gathered therefrom is used by control device 54 in various ways to aid in the operation of the printer, whether in a real-time feedback loop, an offline calibration process, a registration system, etc.

Typically, a printer using control systems which rely on monitors such as 56, 52 require the deliberate creation of what shall be here generally called "test patches" which are made and subsequently measured in various ways by one or another monitor. These test marks may be in the form of test patches of a desired darkness value, a desired color blend, or a particular shape, such as a line pattern; or they may be of a shape particularly useful for determining registration of superimposed images ("fiducial" or "registration" marks). Various image-quality systems, at various times, will require test marks of specific types to be placed on photoreceptor 210 at specific locations. These test marks will be made on photoreceptor 210 by one or more lasers such as 14C, 14M, 14Y, and 14K. Printing process may be controlled, for example, by a print controller 200.

As is familiar in the art of "laser printing," by coordinating the modulation of the various lasers with the motion of photoreceptor 210 and other hardware (such as rotating mirrors, etc., not shown), the lasers discharge areas on photoreceptor 210 to create the desired test marks, particularly after these areas are developed by their respective development units 16C, 16M, 16Y, 16K. The test marks must be placed on the photoreceptor 210 in locations where they can be subsequently measured by a (typically fixed) monitor elsewhere in the printer, for whatever purpose.

In an embodiment, the linear sensor array 2, as described above, can be placed just before or just after the transfer station 20 where the toner is transferred to the sheet, for example, on monitors such as 56, 58. In another embodiment, the linear sensor array 2, may be placed directly on a printed sheet as the printed sheet comes out of the machine, for example, on monitor such as 52.

While the specific embodiments of the present disclosure have been described above, it will be appreciated that the disclosure may be practiced otherwise than described. The description is not intended to limit the disclosure.

What we claim is:

1. A printer or electronic copier, comprising:
    a print engine configured to apply a marking medium to an image bearing surface to form a printed image on an output media;
    a system for providing specular reflectance of the image bearing surface in the printer or electronic copier, the system comprising:
        (i) an illuminator array positioned adjacent to the image bearing surface, the illuminator array comprising a plurality of discrete illuminator elements spaced in a linear arrangement, the illuminating elements each being configured to emit a light beam;
        (ii) a lens array comprising a plurality of collimator lenses positioned between the illuminator array and the image bearing surface, the collimator lenses being positioned with respect to the illuminator array to receive the light beams emitted by the illuminator elements and to collimate the light beams for transmission to the image bearing surface at an incidence angle; and
        (iii) a linear sensor array comprising a plurality of sensors positioned adjacent to the image bearing surface such that specular and diffuse portions of the collimated light beams reflecting off the image bearing surface at a reflectance angle are received by the sensors.

2. The printer or electronic copier of claim 1, wherein the illuminator array comprises a linear LED array, wherein each discrete illuminator comprises an LED.

3. The printer or electronic copier of claim 1, wherein the image bearing surface is on a photoreceptor comprising a belt or a drum.

4. The printer or electronic copier of claim 1, further comprising a lens placed in the optical path of the light beams reflecting off the image bearing surface at the reflectance angle.

5. The printer or electronic copier of claim 4, wherein the lens is a gradient index lens.

6. The printer or electronic copier of claim 1, wherein the linear sensor array is a full width array (FWA) sensor, contact image sensor, CMOS array sensor or a CCD array sensor.

7. The printer or electronic copier of claim 1, further comprising a processor configured to process the specular and the diffuse portions of the light beams reflecting off the image bearing surface and detected by the linear sensor array.

8. The printer or electronic copier of claim 1, wherein the marking medium is toner or ink.

9. A method for providing the specular reflectance of an image bearing surface in a printer or electronic copier, the method comprising:
    forming a printed image on an output media by applying a marking medium to the image bearing surface;
    emitting light beams from discrete illuminator elements of an illuminator array comprising a plurality of the discrete illuminator elements spaced in a linear arrangement adjacent to the image bearing surface;
    positioning a lens array comprising a plurality of collimator lenses between the illuminator array and the image bearing surface;
    collimating the emitted light beams with a plurality of collimator lenses positioned between the illuminator array and the image bearing surface, the collimator lenses being positioned with respect to the illuminator array to receive and collimate the lights beams for transmission to the image bearing surface at an incidence angle; and
    receiving specular portions and diffuse portions of the collimated light beams reflecting off the image bearing surface at a reflectance angle with a plurality of sensors comprising a linear sensor array adjacent to the image bearing surface.

10. The method of claim 9, further comprising processing the specular and the diffuse portions of the light beams reflecting off the image bearing surface and detected by the linear sensor array.

11. The method of claim 9, wherein the illuminator array comprises a linear LED array, wherein each discrete illuminator comprises an LED.

12. The method of claim 9, wherein the image bearing surface is on a photoreceptor comprising a belt or a drum.

13. The method of claim 9, further comprising using a lens placed in the optical path of the light beams reflecting off the image bearing surface at the reflectance angle.

14. The method of claim 13, wherein the lens is a gradient index lens.

15. The method of claim 9, wherein the linear sensor array is a full width array (FWA) sensor, contact image sensor, CMOS array sensor or a CCD array sensor.

16. The method of claim 9, wherein the marking medium is toner or ink.

* * * * *